(12) United States Patent
Nana et al.

(10) Patent No.: US 10,648,018 B2
(45) Date of Patent: May 12, 2020

(54) REACTION VESSEL SYSTEMS AND METHODS AND SYSTEMS FOR USING SAME

(71) Applicant: Abbott Molecular Inc., Des Plaines, IL (US)

(72) Inventors: Sonal Sadaria Nana, Chicago, IL (US); Paul M. Grippo, Abbott Park, IL (US); Eric D. Yeaton, Epsom, NH (US); Jason E. Bryant, Eliot, ME (US); Mark Talmer, Pepperell, MA (US); Kavankumar B. Patel, Mount Prospect, IL (US); Wesley W. Addison, II, Chicago, IL (US)

(73) Assignee: Abbott Molecular Inc, Des Plaines, IL (US)

( * ) Notice: Subject to any disclaimer, the term of this patent is extended or adjusted under 35 U.S.C. 154(b) by 373 days.

(21) Appl. No.: 15/460,188

(22) Filed: Mar. 15, 2017

(65) Prior Publication Data
US 2017/0268039 A1 Sep. 21, 2017

Related U.S. Application Data

(60) Provisional application No. 62/308,620, filed on Mar. 15, 2016.

(51) Int. Cl.
| | |
|---|---|
| *B01L 3/00* | (2006.01) |
| *C12Q 1/6806* | (2018.01) |
| *B01L 7/00* | (2006.01) |
| *C12Q 1/6844* | (2018.01) |
| *G01N 35/10* | (2006.01) |

(52) U.S. Cl.
CPC ............ *C12Q 1/6806* (2013.01); *B01L 3/508* (2013.01); *B01L 7/52* (2013.01); *C12Q 1/6844* (2013.01); *G01N 35/10* (2013.01); *B01L 2200/026* (2013.01); *B01L 2200/0689* (2013.01); *B01L 2300/042* (2013.01); *B01L 2300/0848* (2013.01); *G01N 2035/1034* (2013.01)

(58) Field of Classification Search
CPC ... B01L 3/50825; B01L 3/50853; B01L 3/523
USPC ........................................ 422/549, 547, 558
See application file for complete search history.

(56) References Cited

U.S. PATENT DOCUMENTS

| | | |
|---|---|---|
| 5,846,489 A | 12/1998 | Bienhaus et al. |
| 2004/0067169 A1 | 4/2004 | Krause |
| 2004/0106097 A1 | 6/2004 | Huffer et al. |

(Continued)

*Primary Examiner* — Natalia Levkovich
(74) *Attorney, Agent, or Firm* — Edward J. Baba; Bozicevic, Field & Francis LLP

(57) ABSTRACT

Aspects of the present disclosure include systems that include reaction vessels and reaction vessel caps. In certain aspects, the reaction vessels include a reaction chamber and a groove disposed around a top opening of a reaction chamber. The system also includes a RV cap that includes a cap body, a RV plug, and a lower wall that includes an outer radial groove disposed above an outward projecting ridge of the lower wall. When the cap is inserted into the RV, the RV plug of the RV cap is sealingly inserted into the reaction chamber of the RV, a ridge of the RV mates with the outer radial groove of the RV cap, and an outward projecting ridge of the RV cap mates with the radial groove of the RV. Also provided are methods and sample analysis systems, which may employ the RV/RV cap systems of the present disclosure.

26 Claims, 10 Drawing Sheets

(56) References Cited

U.S. PATENT DOCUMENTS

| | | |
|---|---|---|
| 2005/0013742 A1 | 1/2005 | Shaw |
| 2007/0183937 A1 | 8/2007 | Sarstedt |
| 2014/0272989 A1* | 9/2014 | Knight ................ B01L 3/50825 435/6.12 |
| 2016/0023211 A1 | 1/2016 | Knight |

* cited by examiner

US 10,648,018 B2

REACTION VESSEL SYSTEMS AND METHODS AND SYSTEMS FOR USING SAME

CROSS-REFERENCE TO RELATED APPLICATIONS

This application claims the benefit of U.S. Provisional Patent Application No. 62/308,620 filed Mar. 15, 2016, which application is incorporated herein by reference in its entirety.

INTRODUCTION

Certain applications in the field of chemical processing benefit from precise control of the temperature of reaction mixtures, such as biological samples mixed with chemicals and/or reagents. Certain such applications also benefit from the ability to detect target analytes and to induce rapid temperature changes in the mixtures. Applications for heat-exchanging chemical reactions encompass organic, inorganic, biochemical and molecular reactions, and the like. Examples of thermal chemical reactions include thermal cycling nucleic acid amplification, such as the polymerase chain reaction (PCR), isothermal nucleic acid amplification, ligase chain reaction (LCR), self-sustained sequence replication, homogeneous ligand binding assays, enzyme kinetic studies, biochemical mechanistic studies that require complex temperature changes, and the like. Temperature control systems also enable the study of certain physiologic processes where a constant and accurate temperature is required.

One use of temperature control systems is for performing polymerase chain reaction (PCR), which involves the amplification of a nucleic acid segment. According to this methodology, a nucleic acid template is used with a thermostable DNA polymerase, nucleoside triphosphates, and two primers (i.e., oligonucleotides with different sequences, complementary to sequences that lie on opposite strands of the template nucleic acid and which flank the segment of nucleic acid that is to be amplified). The reaction components are cycled between a first temperature (e.g., 95° C.) for denaturing double stranded template nucleic acid, followed by a second temperature (e.g., 40-60° for annealing of primers, and a third temperature (e.g., 70-75° C.) for polymerization. In certain assays, the annealing and polymerization may be performed at the same temperature, so that only two temperatures are required in each thermal cycle. Repeated cycling provides exponential amplification of the template nucleic acid.

SUMMARY

Aspects of the present disclosure include systems that include reaction vessels and reaction vessel caps. In certain aspects, the reaction vessels include a reaction chamber and a groove disposed around a top opening of a reaction chamber. The system also includes a RV cap that includes a cap body, a RV plug, and a lower wall that includes an outer radial groove disposed above an outward projecting ridge of the lower wall. When the cap is inserted into the RV, the RV plug of the RV cap is sealingly inserted into the reaction chamber of the RV, a ridge of the RV mates with the outer radial groove of the RV cap, and an outward projecting ridge of the RV cap mates with the radial groove of the RV. Also provided are methods and sample analysis systems, which may employ the RV/RV cap systems of the present disclosure.

DETAILED DESCRIPTION

Figure 1:
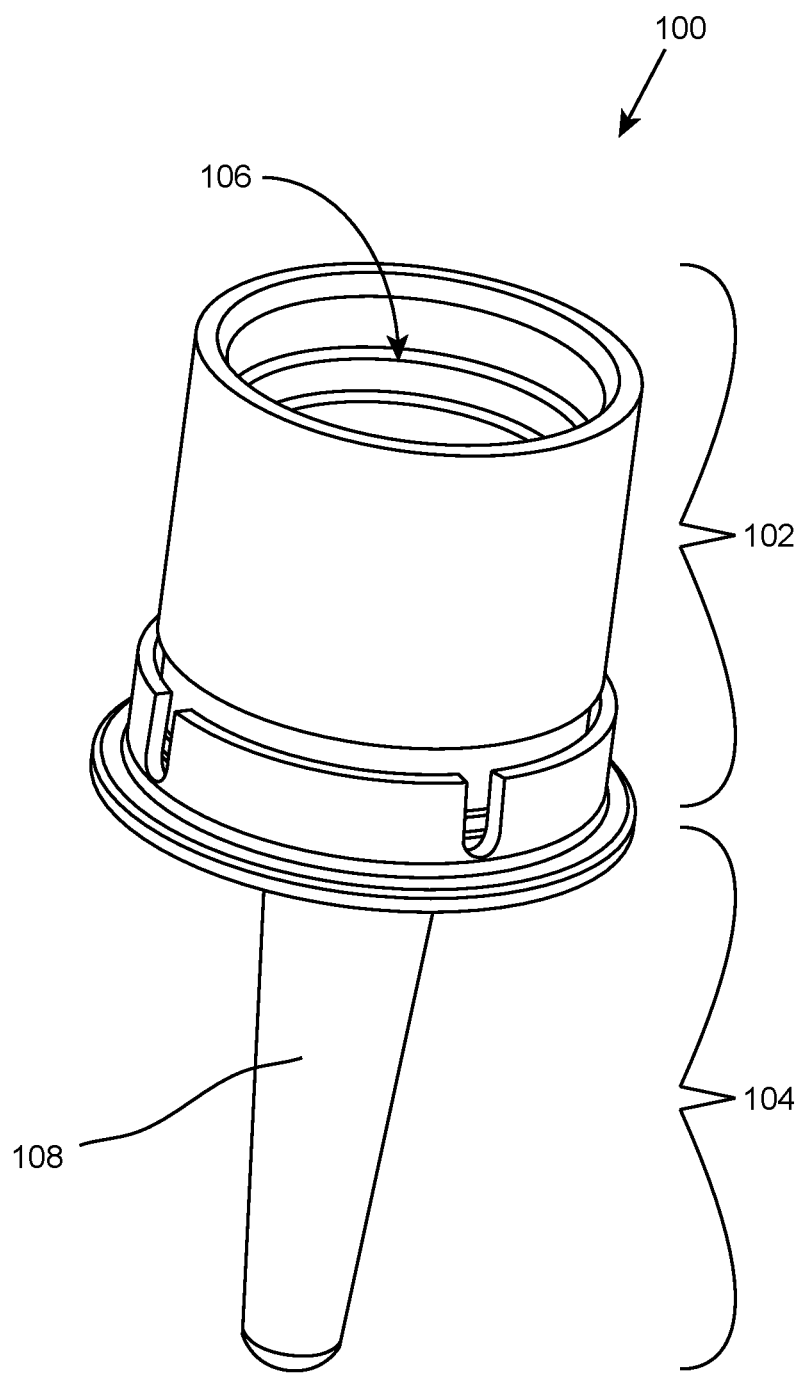
FIG. 1 shows an external view of a reaction vessel (RV) and RV cap mated to each other according to one embodiment of the present disclosure.

Aspects of the present disclosure include systems that include reaction vessels and reaction vessel caps. In certain aspects, the reaction vessels include a reaction chamber and a groove disposed around a top opening of a reaction chamber. The system also includes a RV cap that includes a cap body, a RV plug, and a lower wall that includes an outer radial groove disposed above an outward projecting ridge of the lower wall. When the cap is inserted into the RV, the RV plug of the RV cap is sealingly inserted into the reaction chamber of the RV, a ridge of the RV mates with the outer radial groove of the RV cap, and an outward projecting ridge of the RV cap mates with the radial groove of the RV. Also provided are methods and sample analysis systems, which may employ the RV/RV cap systems of the present disclosure.

Before the present systems and methods are described in greater detail, it is to be understood that the present disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the present systems and methods. The upper and lower limits of these smaller ranges may independently be included in the smaller ranges and are also encompassed within the systems and methods, subject to any specifically excluded limit in the stated range. Where the stated range includes one or both of the limits, ranges excluding either or both of those included limits are also included in the systems and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present systems and methods, representative illustrative sample systems and methods are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present systems and methods. Any recited method can be carried out in the order of events recited or in any other order which is logically possible.

Reaction Vessel Systems

As summarized above, aspects of the present disclosure include reaction vessel systems. According to certain embodiments, the systems include a reaction vessel (RV) and a RV cap. The RV cap may include an RV plug for sized for insertion into and sealing of a reaction chamber of the RV. In addition to mating via the RV plug, the RV and RV cap may include additional features for securably attaching to one another. For example, the RV cap and the RV may be configured such that when the RV cap is inserted into the RV, a ridge of a groove of the RV cap inserts into a groove of the RV, a ridge of a groove of the RV inserts into a groove of the RV cap, or both. In certain aspects, the attachment features secure (e.g., lock, clasp, hook, snap cap, screw cap, and the like) a seal formed between the reaction chamber of the RV and the RV plug of the RV cap. Such securing/locking is particularly useful in the context of containing reaction mixtures subjected to high temperatures (e.g., those subjected to thermocycling for nucleic acid amplification), to reduce or eliminate the possibility of the seal between the reaction chamber of the RV and the RV plug of the RV cap being compromised at high temperature and, accordingly, high pressure. The seal being compromised may result in a number of undesirable consequences, such as contamination of the surrounding area with analytes present in the reaction mixture, evaporation of the reaction mixture, and/or the like.

According to certain embodiments, a reaction vessel system of the present disclosure includes a RV and a RV cap. The RV includes a reaction chamber including a top opening and a closed bottom, and a groove disposed around the perimeter of the top opening, the groove including an outer groove wall, the outer groove wall including a radial groove disposed below an inward-projecting ridge on the outer groove wall. The RV cap of such a system includes a cap body including a pipettor barrel interface including an open top and a closed bottom, and a RV plug projecting downward from a central region of the bottom of the cap body, the RV plug sized for insertion into and sealing of the reaction chamber of the RV. The RV cap further includes a lower wall projecting downward from the perimeter of the bottom of the cap body, the lower wall including an outer radial groove disposed above an outward projecting ridge of the lower wall. When the RV cap is fully inserted into the RV, the RV plug of the RV cap is sealingly inserted into the reaction chamber of the RV, the inward-projecting ridge on the outer groove wall of the RV is inserted into the outer radial groove of the RV cap, and the outward projecting ridge of the RV cap is inserted into the radial groove of the RV.

In certain aspects, the RV cap of the system includes a hole in communication with the pipettor barrel interface for venting when a pipettor barrel is inserted into the pipettor barrel interface. That is, the hole is sufficient to relieve the pressure within the pipettor barrel interface when a pipettor barrel is inserted into the pipettor barrel interface.

The top opening of the reaction chamber of the RV may be any convenient shape. In certain aspects, the top opening of the reaction chamber of the RV is circular. The shape of the reaction chamber may vary. According to certain embodiments, the reaction chamber has a conical shape. The bottom of the reaction chamber may be flat. In other aspects, the reaction chamber has a round bottom.

In certain aspects, the wall of the reaction chamber is straight, where by "straight" is meant the wall does not include a "step" (or "ridge"). In other aspects, the wall of the reaction chamber includes one or more (e.g., 2 or more, 3 or more, 4 or more, etc.) steps. The one or more steps may be complementary to the shape of the RV plug of the RV cap. For example, according to certain embodiments, the reaction chamber includes a step that forms an upper region and a lower region of the reaction chamber, where the shape of the upper region is complementary to the shape of the RV plug.

The volume of the reaction chamber may vary. In certain aspects, the reaction chamber is sized to contain a reaction mixture having a volume of from 5 microliters to 1 milliliter. For example, the reaction chamber may be sized to contain a reaction mixture having a volume of from 5 microliters to 500 microliters. According to certain embodiments, the reaction chamber is sized to contain a reaction mixture having a volume of from 5 microliters to 100 microliters.

In certain aspects, when the RV cap is fully inserted into the RV, the fluid capacity of the reaction chamber is 1 mL or less, 750 µL or less, 500 µL or less, 400 µL or less, 300 µL or less, 250 µL or less, 200 µL or less, 150 µL or less, 100 µL or less, 50 µL or less, or 25 µL or less.

The external surface of the RV may include a variety of shapes and features. In certain aspects, the bottom surface of the reaction vessel is round. In other aspects, the bottom surface of the reaction vessel is flat.

As summarized above, the RV cap may include a pipettor barrel interface that includes an open top and a closed bottom. The wall of the pipettor barrel interface may straight. In other aspects, the wall of the pipettor barrel interface includes one or more steps. For example, the pipettor barrel interface may include a step that forms an upper region and a lower region of the interface, where the shape of the upper and/or lower regions of the pipettor barrel interface is complementary to the shape of a pipettor barrel, e.g., a terminal portion of the pipettor barrel that mates with the pipettor barrel interface of the RV cap. In other aspects, the pipettor barrel interface of the RV cap includes one or more steps that provide a top opening that is wider than the terminal portion of the pipettor barrel, such that the top opening provides tolerance for a degree of misalignment between the pipettor barrel and the pipettor barrel interface of the RV cap. The pipettor barrel interface of the RV cap may include a step such that the interface captures on o-ring circumscribing the pipettor barrel, e.g., to facilitate the formation of a seal between the pipettor barrel and the pipettor barrel interface.

The RV plug of the RV cap may be solid. In other aspects, the RV plug of the RV cap includes an internal cavity. The internal cavity increases the volume within the reaction chamber as compared to a solid RV plug.

The RV and RV cap may be independently selected from a material suitable for the application in which the RV system will be employed. In certain aspects, the RV and RV cap are made of a material independently selected from polypropylene, polystyrene, and polycarbonate. According to certain embodiments, the RV and/or RV cap are made of two or more of polypropylene, polystyrene, and polycarbonate.

According to certain embodiments, the RV cap is integrated with the RV. By "integrated" is meant the RV cap and the RV are present as a single piece of material (e.g., plastic). In certain aspects, the RV cap is not integrated with the RV, such that the RV cap and RV are two separate pieces of the material.

In certain aspects, an RV system of the present disclosure includes the RV cap mated to the RV. That is, the RV is capped with the RV cap. According to certain embodiments, an RV system of the present disclosure includes a pipettor barrel mated with the RV cap via the pipettor barrel interface of the RV cap.

An external 3-dimensional view of an RV system according to one embodiment is illustrated in FIG. 1. In this example, RV system 100 includes RV cap 102 mated to RV 104. RV cap 102 includes pipettor barrel interface 106 that includes an open top and closed bottom. The pipettor barrel interface has a shape (or "cavity") that is complementary to the shape of a terminal region of a pipettor barrel. Internal to wall 108 of RV 104 is a reaction chamber suitable for containing a reaction mixture, e.g., a PCR reaction mixture (e.g., a real-time PCR reaction mixture).

Figure 2:
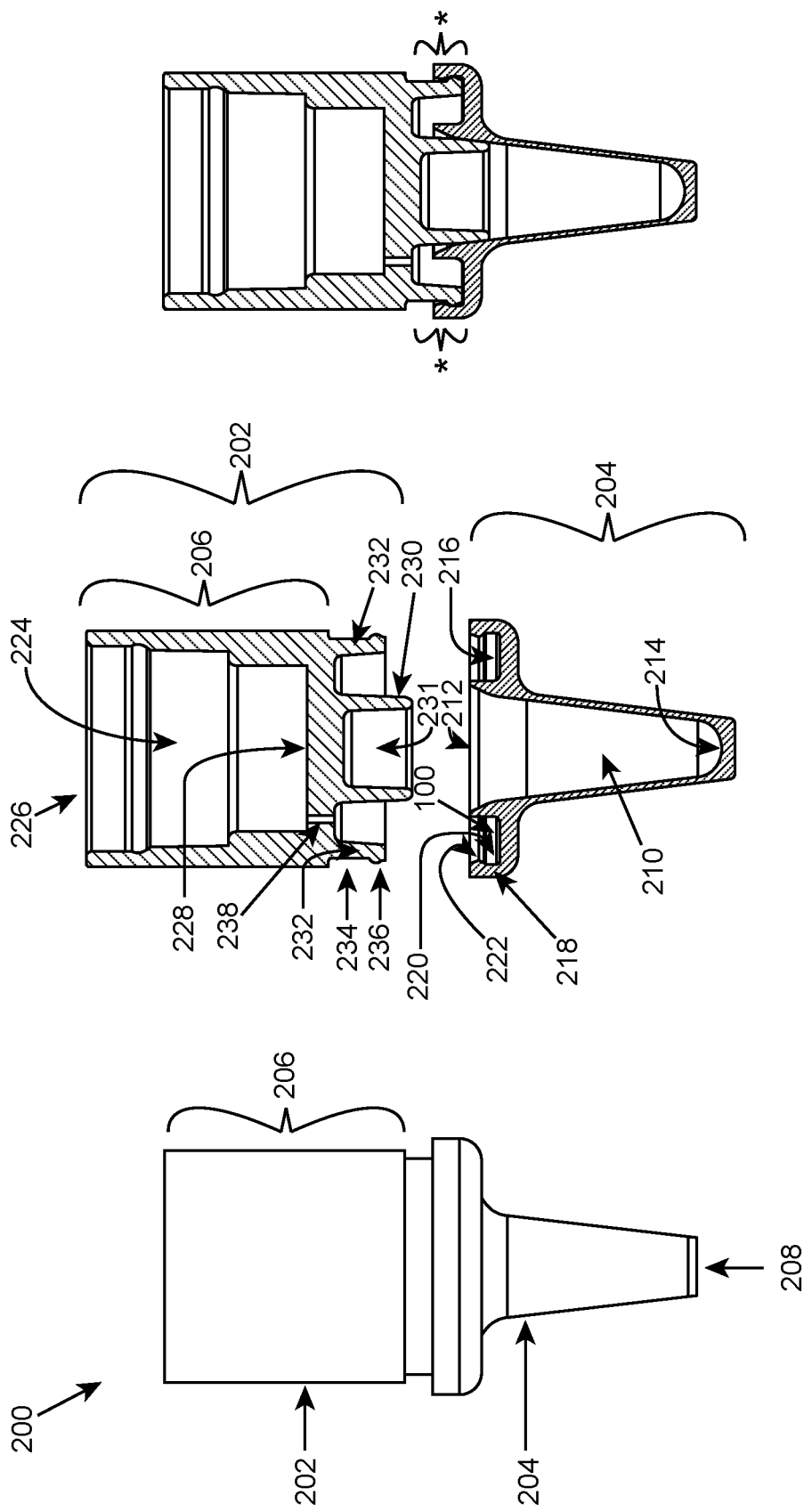
FIG. 2 shows an RV system according to one embodiment of the present disclosure. On the left is an external view of a RV and RV cap mated to each other. In the middle is a cross section view of the RV and RV cap separated from each other. On the right is a cross section view of the RV and RV cap mated to each other.

An RV system according to one embodiment is illustrated in FIG. 2. Shown on the left is an external view of RV system 200 that includes RV cap 202 mated to RV 204. RV cap 202 includes cap body 206. Bottom surface 208 of RV 204 is flat.

Shown in the middle of FIG. 2 is a cross section view of the RV and RV cap in a non-mated state. RV 204 includes reaction chamber 210 that includes top opening 212 and closed bottom 214. In this example, top opening 212 is circular, the reaction chamber is conical in shape, and closed bottom 214 is a round bottom. RV 204 includes groove 216 disposed around the perimeter of the top opening. Groove 216 includes outer groove wall 218 that includes radial groove 220 disposed below inward-projecting ridge 222 on outer groove wall 218.

According to the embodiment shown in FIG. 2, cap body 206 of RV cap 202 includes pipettor barrel interface 224 including open top 226 and closed bottom 228. The shape of pipettor barrel interface 224 is complementary to a terminal portion of a pipettor barrel. RV cap 202 further includes RV plug 230 projecting downward from a central region of the bottom of the cap body 206. RV plug is sized for insertion into and sealing of reaction chamber 210 of RV 204. In this embodiment, RV plug 230 includes internal cavity 231. RV cap 202 includes lower wall 232 projecting downward from the perimeter of the bottom of cap body 206. Lower wall 232 includes outer radial groove 234 disposed above outward projecting ridge 236 of lower wall 232. As shown on the right in FIG. 2, when RV cap 202 is fully inserted into RV 204, RV plug 230 of RV cap 202 is sealingly inserted into reaction chamber 210 of RV 204, inward-projecting ridge 222 is inserted into outer radial groove 234, and outward projecting ridge 236 is inserted into radial groove 220. The insertion of the ridges into the grooves is indicated by asterisks on the right in FIG. 2. In this example, RV cap 202 includes vent hole 238 that connects the space formed between lower wall 232 and RV plug 230 with pipettor barrel interface 224. The vent hole finds use, e.g., to relieve excess air pressure resulting from insertion of the RV cap into the RV. Such a vent hole could be provided in any of the RV systems of the present disclosure.

Figure 3:
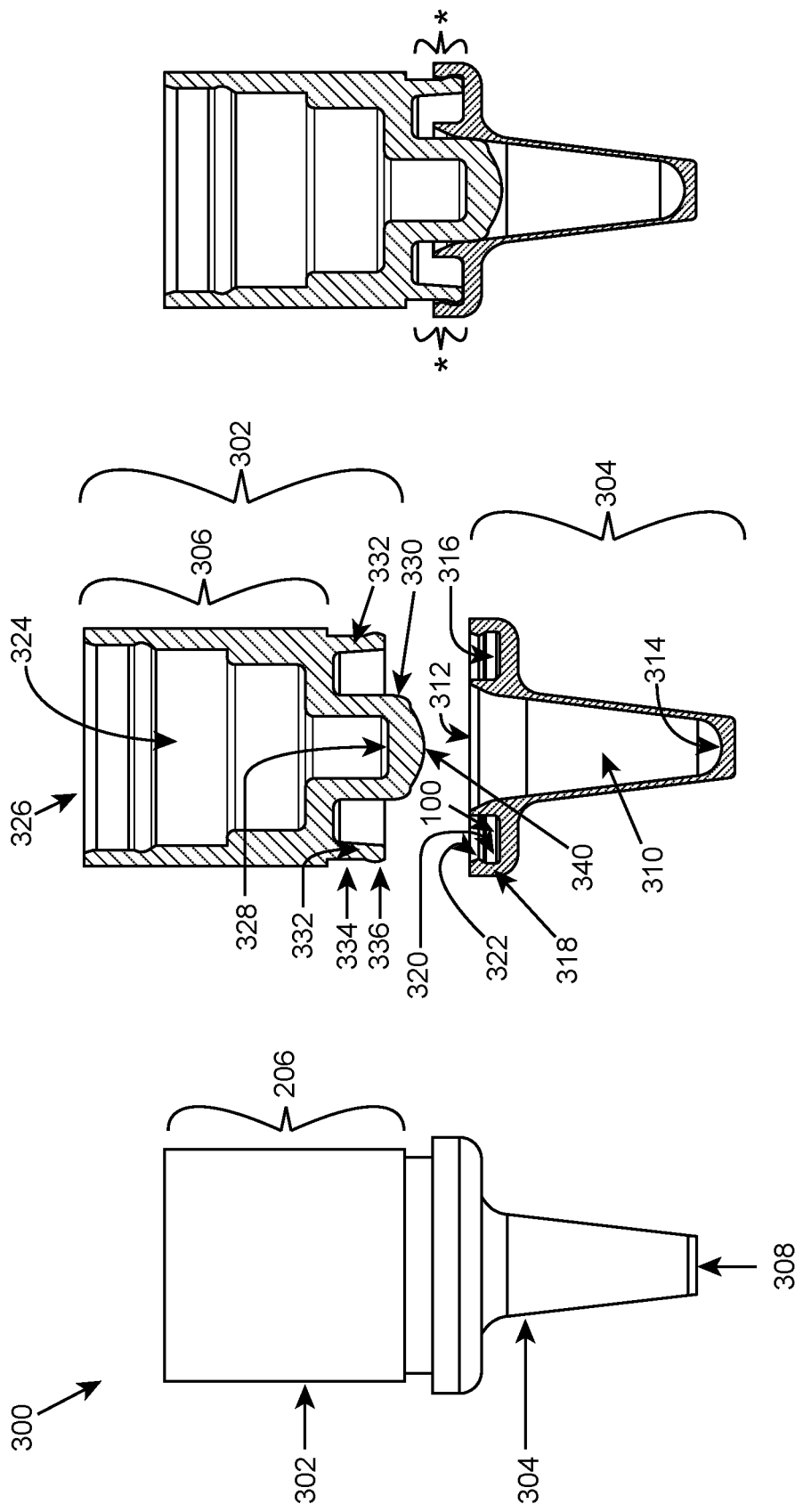
FIG. 3 shows an RV system according to one embodiment of the present disclosure. On the left is an external view of a RV and RV cap mated to each other. In the middle is a cross section view of the RV and RV cap separated from each other. On the right is a cross section view of the RV and RV cap mated to each other.

An RV system according to one embodiment is illustrated in FIG. 3. Shown on the left is an external view of RV system 300 that includes RV cap 302 mated to RV 304. RV cap 302 includes cap body 306. Bottom surface 308 of RV 304 is flat.

Shown in the middle of FIG. 3 is a cross section view of the RV and RV cap in a non-mated state. RV 304 includes reaction chamber 310 that includes top opening 312 and closed bottom 314. In this example, top opening 312 is circular, the reaction chamber is conical in shape, and closed bottom 314 is a round bottom. RV 304 includes groove 316 disposed around the perimeter of the top opening. Groove 316 includes outer groove wall 318 that includes radial groove 320 disposed below inward-projecting ridge 322 on outer groove wall 318.

According to the embodiment shown in FIG. 3, cap body 306 of RV cap 302 includes pipettor barrel interface 324 including open top 326 and closed bottom 328. The shape of pipettor barrel interface 324 is complementary to a terminal portion of a pipettor barrel. RV cap 302 further includes RV plug 330 projecting downward from a central region of the bottom of the cap body 306. RV plug is sized for insertion into and sealing of reaction chamber 310 of RV 304. In this embodiment, RV plug 330 does not include an internal cavity, but rather has lower convex surface 340 so as to reduce the void volume in the reaction chamber of the RV upon insertion of the plug into the RV. In addition, lower convex surface 340 of RV plug 330, upon capping of the RV, displaces or forces the air that makes up the void volume to a circumferential space defined by the lower convex surface 340 of the RV plug and the upper surface of the reaction mixture within the reaction chamber. The inventors have found that the accuracy of real-time PCR assays is improved when the air within the reaction chamber is circumferentially isolated in this manner.

RV cap 302 includes lower wall 332 projecting downward from the perimeter of the bottom of cap body 306. Lower wall 332 includes outer radial groove 334 disposed above outward projecting ridge 336 of lower wall 332. As shown on the right in FIG. 3, when RV cap 302 is fully inserted into RV 304, RV plug 330 of RV cap 302 is sealingly inserted into reaction chamber 310 of RV 304, inward-projecting ridge 322 is inserted into outer radial groove 334, and outward projecting ridge 336 is inserted into radial groove 320. The insertion of the ridges into the grooves is indicated by asterisks on the right in FIG. 3.

In certain aspects, provided is a reaction vessel system that includes a reaction vessel (RV) that includes a reaction chamber including a top opening and a closed bottom. The system further includes a RV cap including a cap body and a RV plug projecting downward from the cap body, the RV plug having a lower convex surface and sized for insertion into and sealing of the reaction chamber of the RV. When the RV cap is inserted into the RV and a reaction mixture is present in the reaction chamber, the lower convex surface of the RV plug reduces the void volume within the reaction chamber and displaces or forces the air that makes up the void volume to a circumferential space defined by the lower convex surface of the RV plug and the upper surface of the reaction mixture within the reaction chamber.

Methods associated with the foregoing embodiment involving an RV plug having a lower convex surface are also provided. In some embodiments, provided are methods of capping a reaction vessel. Such methods include introducing a reaction mixture into a reaction chamber of a RV, and inserting a plug portion of a RV cap into the reaction chamber of the RV. The plug portion of the RV includes a lower convex surface. During the inserting, the lower convex surface of the RV plug reduces the void volume within the reaction chamber and displaces or forces the air that makes up the void volume to a circumferential space defined by the lower convex surface of the RV plug and the upper surface of the reaction mixture within the reaction chamber. As a result the air remains immobilized in the circumferential space defined by the lower convex surface of the RV plug and the upper surface of the reaction mixture during thermal cycling and detection procedures. The immobilization of the air avoids movement of the air during the thermal cycling and detection procedures, which may result in aberrant and/or incorrect readings.

Figure 4:
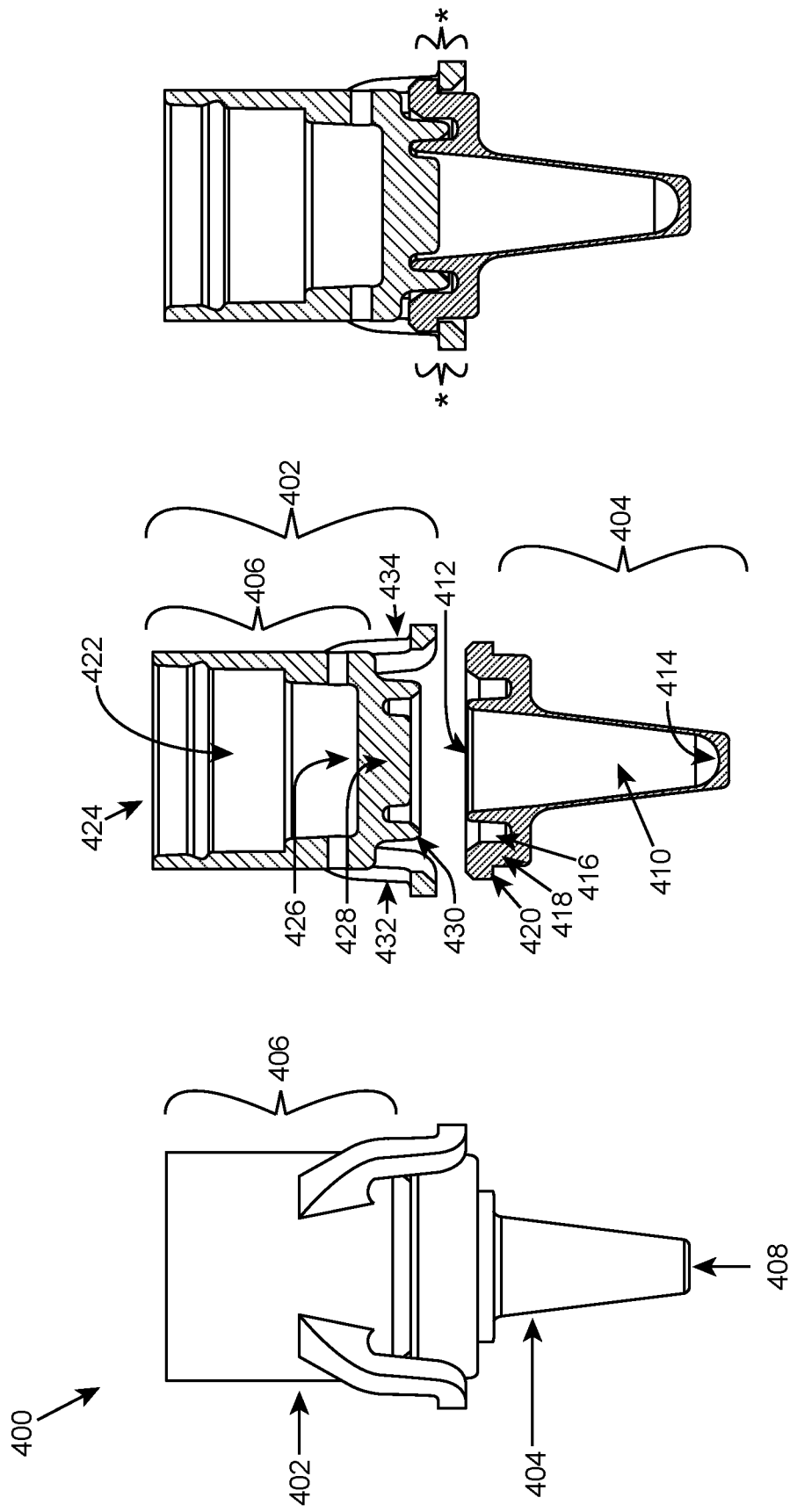
FIG. 4 shows a RV system according to one embodiment of the present disclosure. On the left is an external view of a RV and RV cap mated to each other. In the middle is a cross section view of the RV and RV cap separated from each other. On the right is a cross section view of the RV and RV cap mated to each other.

An RV system according to one embodiment is illustrated in FIG. 4. Shown on the left is an external view of RV system 400 that includes RV cap 402 mated to RV 404. RV cap 402 includes cap body 406. Bottom surface 408 of RV 404 is flat.

Shown in the middle of FIG. 4 is a cross section view of the RV and RV cap in a non-mated state. RV 404 includes reaction chamber 410 that includes top opening 412 and closed bottom 414. In this example, top opening 412 is circular, the reaction chamber is conical in shape, and closed bottom 414 is a round bottom. RV 404 includes groove 416 disposed around the perimeter of the top opening. RV 404 also includes outer groove wall 418 having outward-facing ledge 420.

According to the embodiment shown in FIG. 4, cap body 406 of RV cap 402 includes pipettor barrel interface 422 including open top 424 and closed bottom 426. The shape of pipettor barrel interface 422 is complementary to a terminal portion of a pipettor barrel. RV cap 402 further includes RV plug 428 projecting downward from a central region of the bottom of the cap body 406. RV plug 428 is sized for insertion into reaction chamber 410 of RV 404, but does not seal the reaction chamber when fully inserted. In this embodiment, RV plug 428 is solid (that is, does not include an internal cavity). RV cap 402 includes lower wall 430 projecting downward from the perimeter of the bottom of cap body 406. As shown on the right in FIG. 4, when RV cap 402 is fully inserted into RV 404, RV plug 428 of RV cap 402 is non-sealingly inserted into reaction chamber 410 of RV 404, and lower wall 430 of RV cap 402 is sealingly inserted into groove 416 of RV 404. In addition, RV cap has peripheral clasps 432 and 434 which clasp around outward-facing ledge 420 of RV 404 when RV cap 402 is fully inserted into RV 404, as shown on the right in FIG. 4.

Methods

As summarized above, provided by the present disclosure are methods. In certain aspects, the methods involve the capping of a RV with a RV cap using a pipettor, e.g., using the barrel of a pipettor (e.g., a robotic pipettor). The methods may further include moving the capped RV from a first location to a second location using a pipettor mated to the RV cap of the capped RV via a pipettor barrel interface of the RV cap.

In certain aspects, provided is a method that includes mating a pipettor and a pipette tip by inserting a barrel of the pipettor into a pipettor barrel interface of the pipette tip, dispensing a reaction mixture from the pipette tip mated to the pipettor into a reaction chamber of a reaction vessel (RV), and ejecting the pipette tip from the barrel of the pipettor. The method further includes mating the pipettor and a RV cap by inserting the barrel of the pipettor into a pipettor barrel interface of the RV cap, picking up the RV cap using the pipettor, capping the RV by inserting a plug portion of the RV cap mated to the pipettor into a top opening of the reaction chamber of the RV, and ejecting the RV cap from the barrel of the pipettor to release the capped RV from the pipettor.

According to the method above, subsequent to the capping and prior to ejecting the RV cap from the barrel of the pipettor, the method may include moving the capped RV from a first location to a second location using the pipettor mated to the capped RV. The methods, therefore, may involve a single pipettor (e.g., a robotic pipettor having a single barrel, a robotic multi-channel pipettor, or the like) which not only provides the functionality of aspirating and dispensing reaction mixtures, samples, reagents, and/or the like, but also has the capability of capping an RV and moving the RV.

In certain aspects, subsequent to dispensing the reaction mixture and prior to the capping, the method further includes dispensing a vapor barrier liquid onto the reaction mixture. The vapor barrier liquid may be, e.g., an oil (e.g., mineral oil or other suitable oil). The vapor barrier liquid finds use in preventing evaporation of the reaction mixture when subjected to high temperatures, e.g., thermocycling during PCR amplification.

In certain aspects, the method occurs in a sample analysis system. The sample analysis system may be a clinical chemistry system, an immunoassay system, a nucleic acid analysis system, and/or the like. According to certain embodiments, the methods of the present disclosure are implemented by an automated sample preparation and analysis system. Such a system may be an automated nucleic acid sample preparation and analysis system. Such a system may include a sample analysis unit that is a real-time nucleic acid amplification and detection system. For example, in embodiments that include the moving of a capped RV from a first location to a second location using a pipettor mated to the capped RV, the second location may be a well (e.g., a thermocycler well) disposed in a real-time nucleic acid amplification and detection system. According to such embodiments, the reaction mixture may be a real-time nucleic acid amplification reaction mixture. Reaction mixtures of interest include, but are not limited to, those that find use in a clinical diagnostic application, e.g., to detect/quantify nucleic acids relevant to cancer, nucleic acids indicative of a microbial infection, and/or the like. In certain aspects, the reaction mixture includes real-time nucleic acid amplification reagents and primers designed for the detection/quantification of a nucleic acid target from one or more of human immunodeficiency virus (HIV), Hepatitis C virus (HCV), Hepatitis B virus (HBV), *Chlamydia trachomatis* (CT), *Neisseria gonorrhoeae* (NG), Human papillomavirus (HPV), Cytomegalovirus (CMV), Epstein-Barr virus (EBV), Polyomavirus BK (BKV), Methicillin-resistant *Staphylococcus aureus* (MRSA), *Clostridium difficile* (C. Diff.), Vancomycin-resistant enterococci (VRE), adenovirus, *Mycobacterium tuberculosis* (TB), Varicella Zoster Virus (VZV), Herpes simplex virus (HSV), John Cunningham virus (JCV), enterovirus, Lymphogranuloma Venereum (LGV), viruses of a Respiratory Viral Panel (RVP), Human Herpesvirus 6 (HHV6), *Trichomonas vaginalis, Mycoplasma genitalium*, norovirus, and zika virus.

Figure 5:
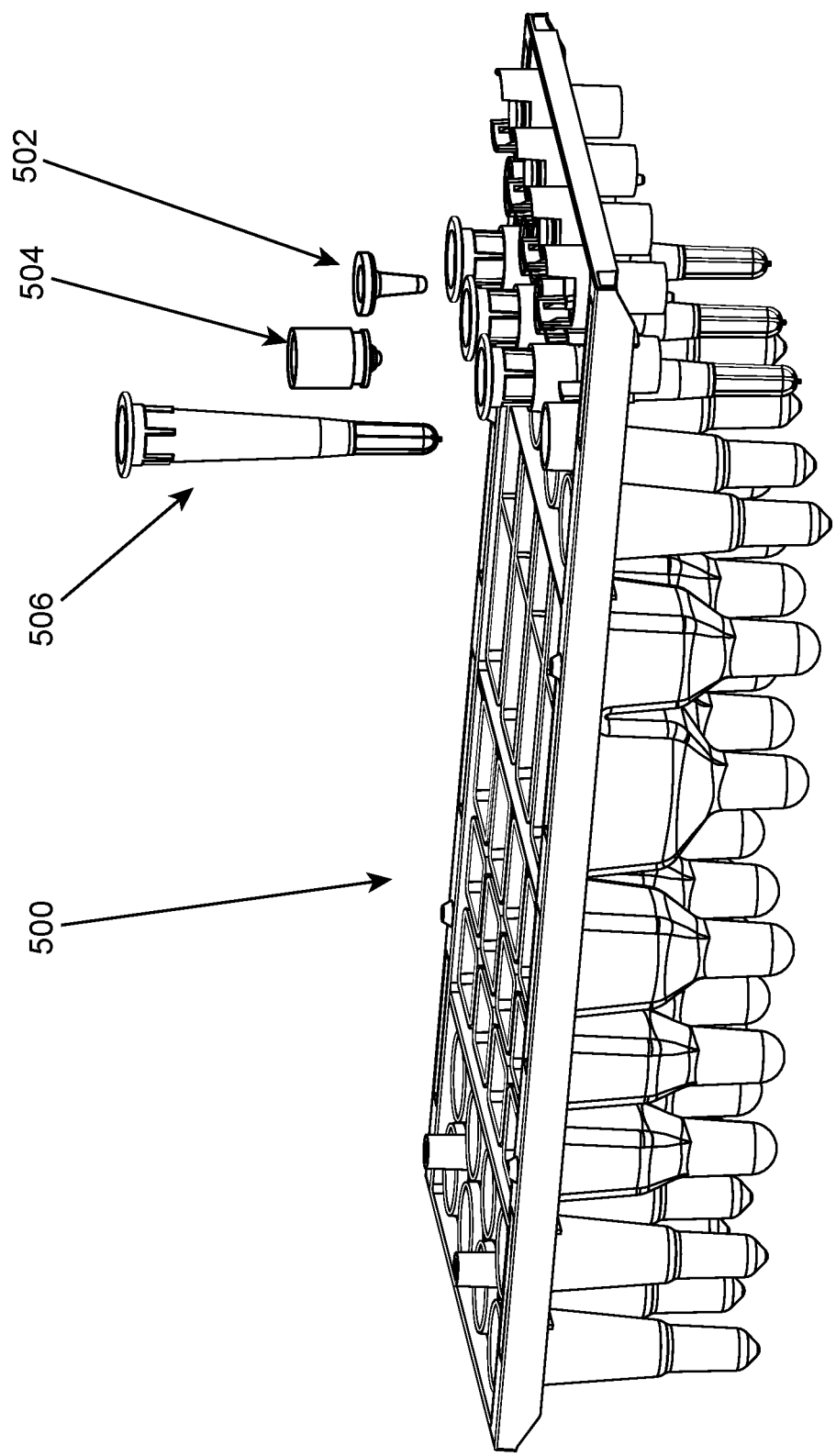
FIG. 5 shows a sample preparation cartridge having openings for holding components of the RV systems of the present disclosure, according to one embodiment.
Figure 6:
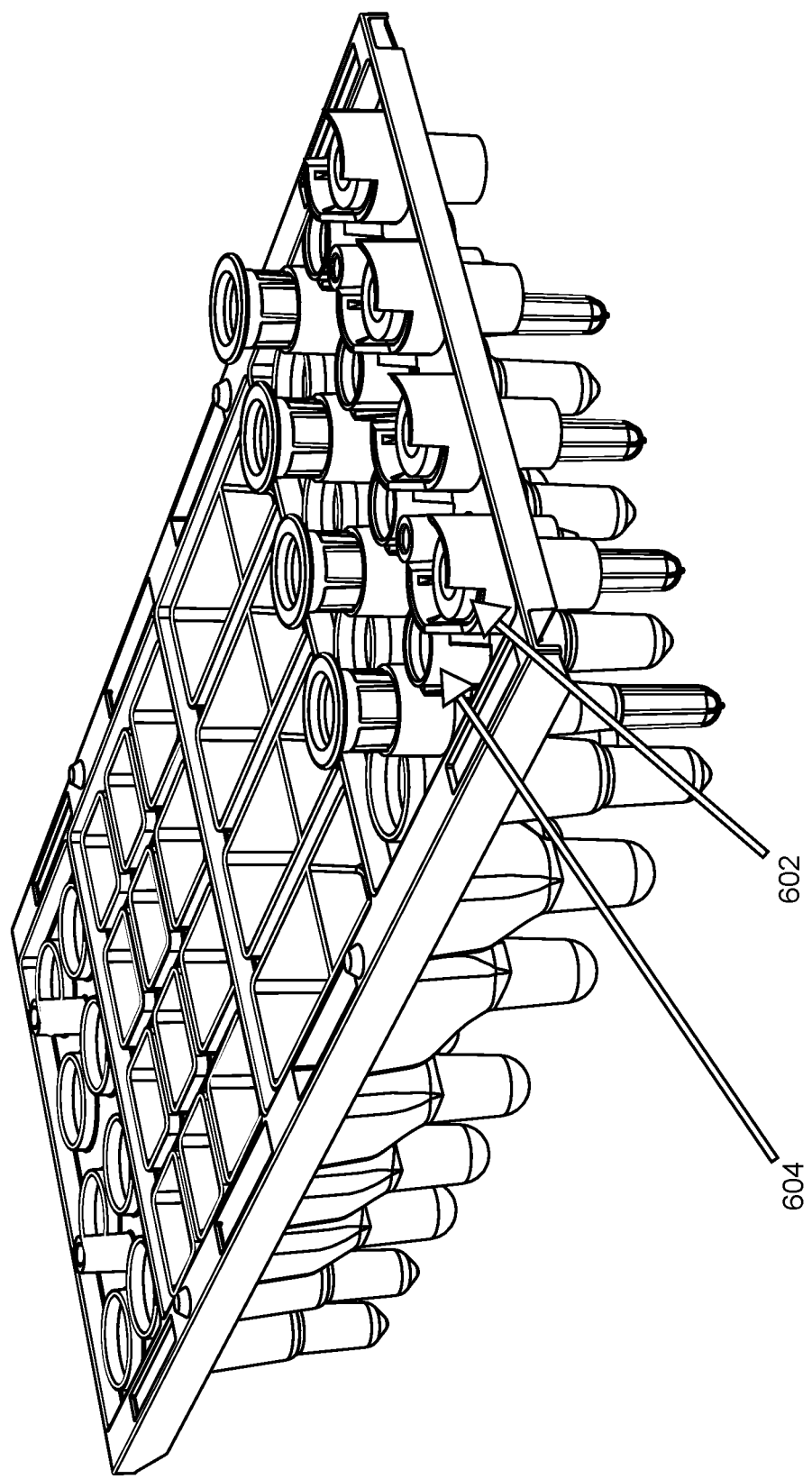
FIG. 6 shows a sample preparation cartridge having openings for holding components of the RV systems of the present disclosure, according to one embodiment.

According to certain embodiments, when the method occurs in a sample analysis system, the first location is a well or opening of a sample preparation cartridge present in the sample analysis system. Such a sample preparation cartridge according to one embodiment is illustrated in FIG. 5. In this example, sample preparation (SP) cartridge 500 has a frame and openings therein for holding RV 502 and RV cap 504 (shown here above their respective openings). Also shown in FIG. 5 is plunger 506 that finds use in a magnetic particle-based nucleic acid isolation and purification procedure that employs the SP cartridge. SP cartridge 500 also includes wells that find use, e.g., in containing sample preparation reagents independently selected from: elution buffer, molecular grade water, nucleic acid wash solution, lysis buffer, pretreatment solution (e.g., for protease incubation with sample), vapor barrier liquid (e.g., an oil) for overlaying on a PCR reaction mixture present in the RV to prevent evaporation during, e.g., thermocycling. When a method of the present invention involves the use of an SP cartridge as shown in FIG. 5, the RV into which the reaction mixture is dispensed may be present in a first opening of the SP cartridge, the RV cap that is picked up by the pipettor may be present in a second opening of the SP cartridge, and the RV is present in the first opening when it is capped by the pipettor. FIG. 6 shows the SP cartridge of FIG. 5, which has 4 lanes of aligned wells and openings, with each lane including a RV cap and an RV, e.g., RV 602 and RV cap 604 positioned in their respective openings.

SP cartridges that may be employed when performing the methods of the present disclosure include those described in, e.g., PCT/US17/22601, which claims priority to U.S. Ser. No. 62/308,618, the disclosures of which are incorporated herein by reference in their entireties.

Figure 7:
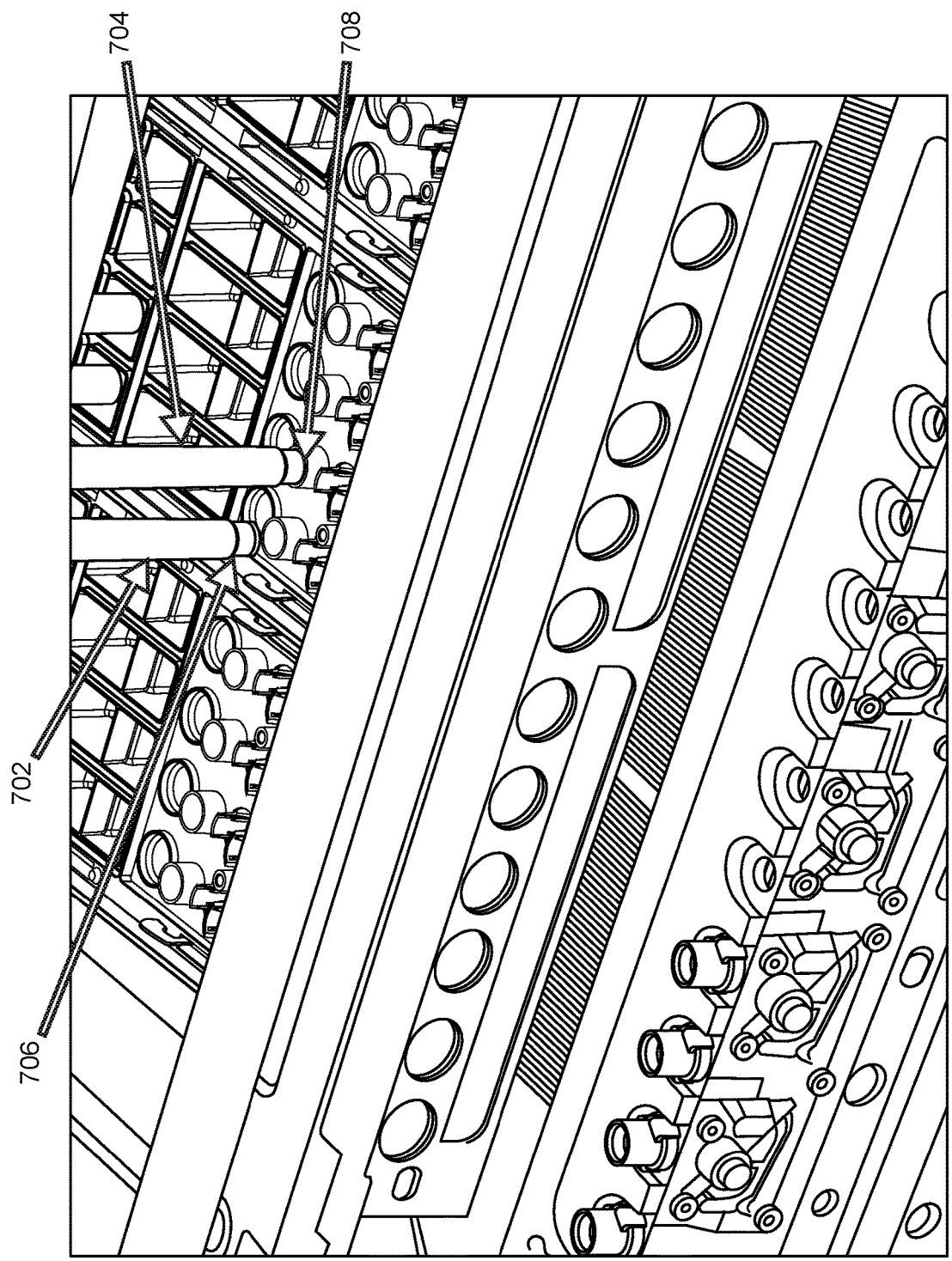
FIG. 7 shows an illustration of a multi-channel robotic pipettor picking up RV caps present in an SP cartridge at a sample preparation unit. Two of the pipettor barrels are mated to respective RV caps in preparation for capping RVs present at adjacent positions of the SP cartridge.
Figure 8:
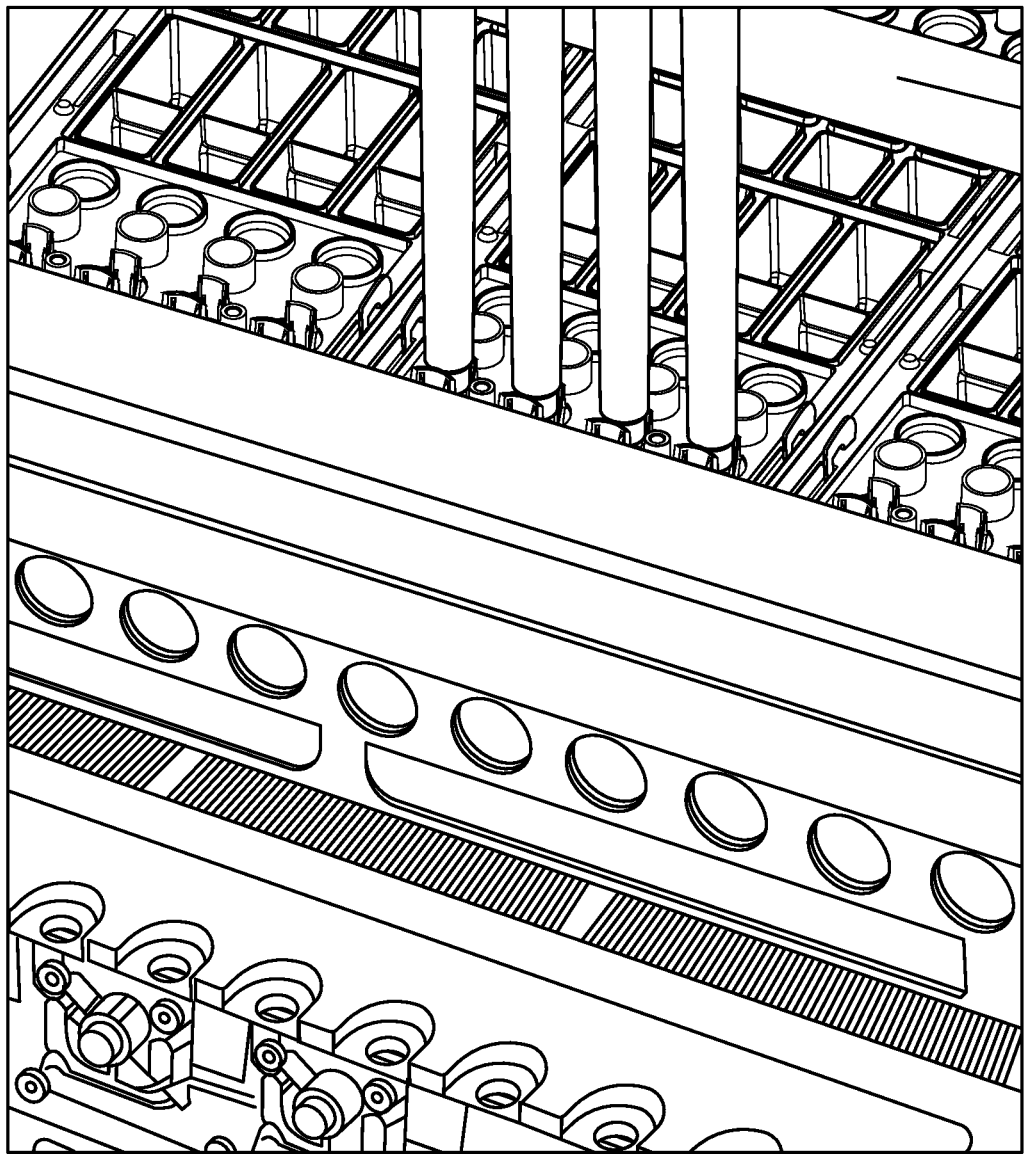
FIG. 8 shows an illustration of the capping of RVs with RV caps by a robotic pipettor according to one embodiment. The pipettor is capping the RVs by inserting a plug portion of the RV caps into a top opening of the reaction chamber of the respective RVs.
Figure 9:
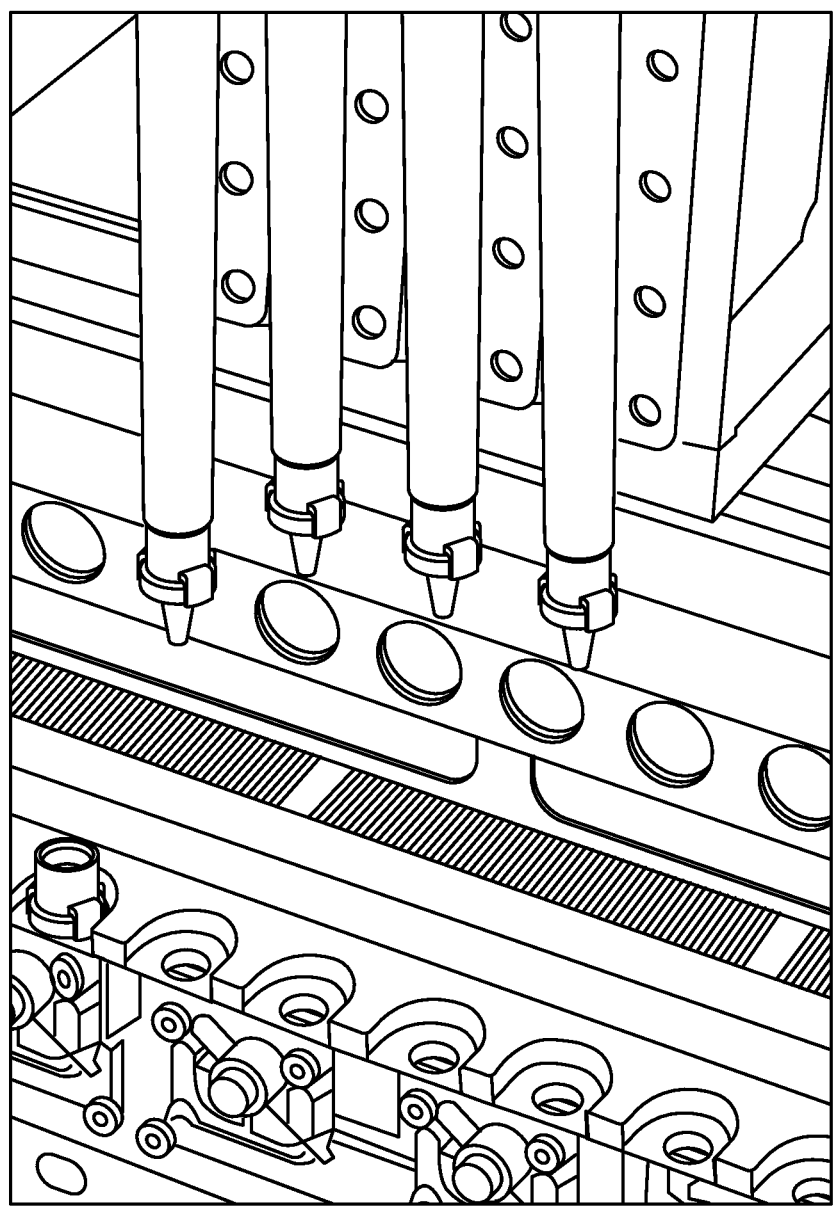
FIG. 9 shows an illustration of the transport of the capped RVs from FIG. 7 from the SP cartridge to RV wells of a sample analysis unit by the robotic pipettor. Terminal portions of the pipettor barrels are mated with the RV caps via pipettor barrel interfaces of the RV caps of the capped RVs, enabling the transport of the capped RVs by the robotic pipettor.

Steps of a method according to one embodiment are shown in FIGS. 7-9. FIG. 7 shows an illustration of a 4-channel robotic pipettor picking up RV caps present in a SP cartridge at a sample preparation unit. Shown are pipettor barrels 702 and 704 of a robotic pipettor mated to RV caps 706 and 708 via pipettor barrel interfaces of the RV caps, in preparation for capping RVs present at adjacent positions of the SP cartridge.

An illustration showing the capping of RVs with RV caps by a robotic pipettor according to one embodiment is provided in FIG. 8. In this example, each of the four barrels of the pipettor are inserting a RV cap into a respective RV in a sample preparation cartridge at a sample preparation unit, to cap the RVs.

FIG. 9 shows the transport of capped RVs from a sample preparation cartridge to RV wells of a sample analysis unit (here, a real-time nucleic acid amplification and detection unit) by the robotic pipettor. The terminal portions of the 4 pipettor barrels are mated with the RV caps of the capped RVs, enabling the transport of the capped RVs by the robotic pipettor.

According to certain embodiments, the methods of the present disclosure may employ an RV cap system of the present disclosure. For example, the RV may include a groove disposed around the perimeter of the top opening, the groove including an outer groove wall, the outer groove wall including a radial groove disposed below an inward-projecting ridge on the outer groove wall. The RV cap may include a cap body including the pipettor barrel interface including an open top and a closed bottom, the plug portion projecting downward from a central region of the bottom of the cap body, the plug portion sized for insertion into and sealing of the reaction chamber of the RV, and a lower wall projecting downward from the perimeter of the bottom of the cap body, the lower wall including an outer radial groove disposed above an outward projecting ridge of the lower wall. According to such embodiments, when the RV is capped, the RV plug of the RV cap is sealingly inserted into the reaction chamber of the RV, the inward-projecting ridge on the outer groove wall of the RV mates with the outer radial groove of the RV cap, and the outward projecting ridge of the RV cap mates with the radial groove of the RV.

Sample Analysis Systems

Also provided by the present disclosure are sample analysis systems. A sample analysis system of the present disclosure may be adapted to perform any of the methods of the present disclosure. The system may include a pipettor (e.g., a robotic pipettor having 1 channel or multiple channels), pipette tips having an interface for interfacing with the barrel(s) of the pipettor, and an RV system that includes RV caps having an interface for interfacing with the barrel(s) of the pipettor, enabling the capping of RVs and movement of capped RVs within the system by the pipettor.

In certain aspects, a sample analysis system of the present disclosure is an automated sample preparation and analysis system. The automated sample preparation and analysis system may include areas for loading samples into the system (e.g., samples present in sample tubes loaded into the system via sample tube racks), loading sample preparation cartridges into the system, loading bulk and other reagents into the system, filling sample preparation cartridges with samples and/or reagents (e.g., using a robotic pipettor of the system), preparing samples (e.g., nucleic acid isolation and purification), and analyzing samples (e.g., by real-time PCR analysis). According to certain embodiments, the automated sample preparation and analysis system is a system described in PCT/US17/22597, which claims priority to U.S. Ser. No. 62/308,617 and U.S. Ser. No. 62/357,772, the disclosures of which are incorporated herein by reference in their entireties.

An automated sample preparation and analysis system of the present disclosure may be an automated nucleic acid sample preparation and analysis system. In certain aspects, when the system is an automated nucleic acid sample preparation and analysis system, the system includes a sample analysis unit that includes a thermocycler. For example, the sample analysis unit of such a system may be a real-time nucleic acid amplification and detection system. Real-time nucleic acid amplification and detection systems that find use in the systems of the present disclosure include those described, e.g., in PCT/US17/22588, which claims priority to U.S. Ser. No. 62/308,632, the disclosures of which are incorporated herein by reference in their entireties.

Figure 10:
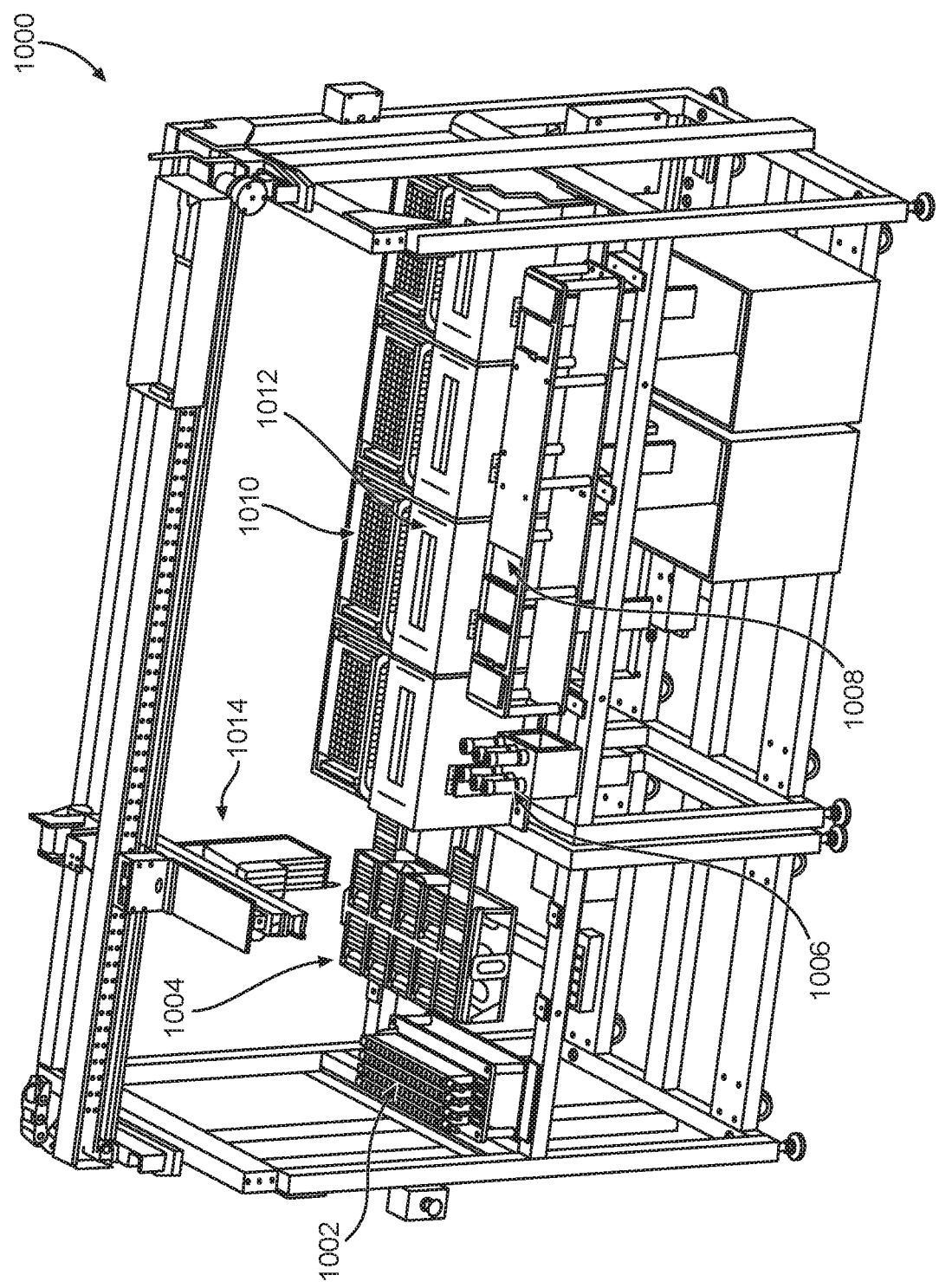
FIG. 10 shows an automated analysis system according to one embodiment of the present disclosure.

An automated sample preparation and analysis system according to one embodiment is shown in FIG. 10. Automated sample analysis system 1000 includes sample loading area 1002, pipette tip loading area 1004, ancillary reagent loading area 1006, assay reagent tray loading area 1008, four sample preparation units (e.g., sample preparation unit 1010) and four sample analysis units, e.g., sample analysis unit 1012. Robotic pipettor 1014 is movable in the X, Y and Z axes (e.g., via drive/servo motor assemblies) to interact with each of the aforementioned system areas/stations. Pipette tips and RV caps present in the system have pipettor barrel interfaces that enable the pipettor to pick up and move pipette tips, pick up and move RV caps, cap RVs with the RV caps, and move capped RVs, with the system. For example, robotic pipettor 1014 can pick up a pipette tip at pipette tip loading area 1004, move to sample loading area 1002, aspirate a sample from a sample tube, move to an SP cartridge present at sample preparation unit 1010, dispense the sample into a well of the SP cartridge, move to a pipette tip disposal area, and eject the used pipette tip into the disposal area. In certain aspects, robotic pipettor 1014 can also dispense a reaction mixture into an RV present in an opening of the SP cartridge present at sample preparation unit 1010, eject the used pipette tip into the disposal area, move back to the SP cartridge, pick up a RV cap present in an opening of the SP cartridge, and cap the RV with the RV cap, e.g., by inserting a plug portion of the RV cap mated to the pipettor into a top opening of the reaction chamber of the RV. According to certain embodiments, robotic pipettor 1014 can also pick up the capped RV and move the capped RV to a well of sample analysis unit 1012, which may be a well of a thermocycler of a real-time nucleic acid amplification and detection unit. The system according to the embodiment shown in FIG. 10 may include and employ any of the reaction vessel systems described herein.

In certain aspects, a system of the present disclosure may include a reaction vessel system of the present disclosure. For example, the system may include any of the RV systems described herein, a robotic pipettor, and a plurality of pipette tips, each of the plurality of pipette tips including a pipettor barrel interface sized and shaped to mate with a barrel of the pipettor. The pipettor barrel interface of the RV cap may resemble the pipettor barrel interface of each of the plurality of pipette tips. The robotic pipettor of the system may be a single channel pipettor, or may be a multi-channel pipettor. For example, the robotic pipettor may include from 1 to 10 pipettor barrels, e.g., from 1 to 8 pipettor barrels, such as from 1 to 4 pipettor barrels. According to one embodiment, the pipettor is a four-channel robotic pipettor.

Notwithstanding the appended claims, the disclosure is also defined by the following clauses:

1. A reaction vessel system, comprising:
   a reaction vessel (RV) comprising:
   a reaction chamber comprising a top opening and a closed bottom;
   a groove disposed around the perimeter of the top opening, the groove comprising an outer groove wall, the outer groove wall comprising a radial groove disposed below an inward-projecting ridge on the outer groove wall;
   a RV cap comprising:
   a cap body comprising a pipettor barrel interface comprising an open top and a closed bottom;
   a RV plug projecting downward from a central region of the bottom of the cap body, the RV plug sized for insertion into and sealing of the reaction chamber of the RV;
   a lower wall projecting downward from the perimeter of the bottom of the cap body, the lower wall comprising an outer radial groove disposed above an outward projecting ridge of the lower wall,
   wherein, when the RV cap is fully inserted into the RV:
   the RV plug of the RV cap is sealingly inserted into the reaction chamber of the RV;
   the inward-projecting ridge on the outer groove wall of the RV is inserted into the outer radial groove of the RV cap; and
   the outward projecting ridge of the RV cap is inserted into the radial groove of the RV.

2. A reaction vessel system, comprising:
   a reaction vessel (RV) comprising:
   a reaction chamber comprising a top opening and a closed bottom;
   a groove disposed around the perimeter of the top opening; and
   an outer groove wall having an outward-facing ledge;
   a RV cap comprising:
   a cap body comprising a pipettor barrel interface comprising an open top and a closed bottom;
   a RV plug projecting downward from a central region of the bottom of the cap body, the RV plug sized for insertion into the reaction chamber of the RV;
   a lower wall projecting downward from the perimeter of the bottom of the cap body,
   wherein, when the RV cap is fully inserted into the RV:
   the RV plug of the RV cap is non-sealingly inserted into the reaction chamber of the RV; and
   the lower wall of the RV cap is sealingly inserted into the groove of the RV.

3. The reaction vessel system of Clause 1 or Clause 2, wherein the top opening of the RV is circular.

4. The reaction vessel system of any one of Clauses 1 to 3, wherein the reaction chamber is conical.

5. The reaction vessel system of any one of Clauses 1 to 4, wherein the reaction chamber has a round bottom.

6. The reaction vessel system of any one of Clauses 1 to 5, wherein the reaction chamber comprises a step that forms an upper region and a lower region of the reaction chamber, wherein the shape of the upper region is complementary to the shape of the RV plug.

7. The reaction vessel system of any one of Clauses 1 to 6, wherein the reaction chamber is sized to contain a reaction mixture having a volume of from 5 microliters to 1 milliliter.

8. The reaction vessel system of Clause 7, wherein the reaction chamber is sized to contain a reaction mixture having a volume of from 5 microliters to 500 microliters.

9. The reaction vessel system of Clause 8, wherein the reaction chamber is sized to contain a reaction mixture having a volume of from 5 microliters to 100 microliters.

10. The reaction vessel system of any one of Clauses 1 to 9, wherein the bottom surface of the reaction vessel is flat.

11. The reaction vessel system of any one of Clauses 1 to 10, wherein the pipettor barrel interface comprises a step that forms an upper region and a lower region of the interface, wherein the shape of the upper and lower regions is complementary to the shape of a pipettor barrel.

12. The reaction vessel system of any one of Clauses 1 to 11, wherein the RV plug comprises an internal cavity.

13. The reaction vessel system of any one of Clauses 1 to 11, wherein the RV plug has a lower convex surface.

14. The reaction vessel system of Clause 13, wherein when the RV cap is inserted into the RV and a reaction mixture is present in the reaction chamber:
the lower convex surface of the RV plug reduces the void volume within the reaction chamber and displaces the air that makes up the void volume to a circumferential space defined by the lower convex surface of the RV plug and the upper surface of the reaction mixture within the reaction chamber 15. The reaction vessel system of any one of Clauses 1 to 14, wherein the RV cap is not integrated with the RV.

16. The reaction vessel system of any one of Clauses 1 to 15, wherein the RV cap is mated to the RV.

17. The reaction vessel system of any one of Clauses 1 to 16, comprising a pipettor barrel mated with the pipettor barrel interface of the RV cap.

18. A method, comprising:
mating a pipettor and a pipette tip by inserting a barrel of the pipettor into a pipettor barrel interface of the pipette tip;
dispensing a reaction mixture from the pipette tip mated to the pipettor into a reaction chamber of a reaction vessel (RV);
ejecting the pipette tip from the barrel of the pipettor;
mating the pipettor and a RV cap by inserting the barrel of the pipettor into a pipettor barrel interface of the RV cap;
picking up the RV cap using the pipettor;
capping the RV by inserting, using the pipettor, a plug portion of the RV cap into a top opening of the reaction chamber of the RV; and
ejecting the RV cap from the barrel of the pipettor to release the capped RV from the pipettor.

19. The method according to Clause 18, wherein subsequent to the capping and prior to the ejecting, the method further comprises moving the capped RV from a first location to a second location using the pipettor mated to the capped RV.

20. The method according to Clause 19, wherein the method occurs in a sample analysis system.

21. The method according to Clause 20, wherein the second location is a well disposed in a sample analysis unit of the sample analysis system.

22. The method according to Clause 21, wherein the sample analysis unit is a real-time nucleic acid amplification and detection system and the reaction mixture is a real-time nucleic acid amplification reaction mixture.

23. The method according to any one of Clauses 20 to 22, wherein the first location is a well or opening of a sample preparation cartridge present in the sample analysis system.

24. The method according to any one of Clauses 18 to 23, wherein subsequent to dispensing the reaction mixture and prior to the capping, the method further comprises dispensing a vapor barrier liquid onto the reaction mixture.

25. The method according to any one of Clauses 18 to 24, wherein:
the RV comprises:
a groove disposed around the perimeter of the top opening, the groove comprising an outer groove wall, the outer groove wall comprising a radial groove disposed below an inward-projecting ridge on the outer groove wall, and
the RV cap comprises:
a cap body comprising the pipettor barrel interface comprising an open top and a closed bottom;
the plug portion projecting downward from a central region of the bottom of the cap body, the plug portion sized for insertion into and sealing of the reaction chamber of the RV; and
a lower wall projecting downward from the perimeter of the bottom of the cap body, the lower wall comprising an outer radial groove disposed above an outward projecting ridge of the lower wall,
wherein, when the RV is capped:
the RV plug of the RV cap is sealingly inserted into the reaction chamber of the RV;
the inward-projecting ridge on the outer groove wall of the RV mates with the outer radial groove of the RV cap; and
the outward projecting ridge of the RV cap mates with the radial groove of the RV.

26. The method according to any one of Clauses 18 to 24, wherein:
the RV comprises:
a groove disposed around the perimeter of the top opening and an outer groove wall having an outward-facing ledge, and
the RV cap comprises:
a cap body comprising the pipettor barrel interface comprising an open top and a closed bottom;
the plug portion projecting downward from a central region of the bottom of the cap body, the plug portion sized for insertion into the reaction chamber of the RV; and
a lower wall projecting downward from the perimeter of the bottom of the cap body,
wherein, when the RV is capped:
the RV plug of the RV cap is non-sealingly inserted into the reaction chamber of the RV; and
the lower wall of the RV cap is sealingly inserted into the groove of the RV.

27. The method according to any one of Clauses 18 to 26, wherein the plug portion of the RV cap has a lower convex surface, and upon inserting the plug portion of the RV cap into the reaction chamber, the lower convex surface of the RV plug reduces the void volume within the reaction chamber and displaces the air that makes up the void volume to a circumferential space defined by the lower convex surface of the RV plug and the upper surface of the reaction mixture within the reaction chamber.

28. A sample analysis system, comprising:
the reaction vessel system of any one of Clauses 1 to 17;

a robotic pipettor; and a plurality of pipette tips, each of the plurality of pipette tips comprising a pipettor barrel interface sized and shaped to mate with a barrel of the pipettor, wherein the pipettor barrel interface of the RV cap resembles the pipettor barrel interface of each of the plurality of pipette tips.

29. The sample analysis system of Clause 28, wherein the robotic pipettor comprises from 1 to 10 pipettor barrels.

30. The sample analysis system of Clause 28 or Clause 29, wherein the system is an automated sample preparation and analysis system.

31. The sample analysis system of Clause 30, wherein the automated sample preparation and analysis system is an automated nucleic acid sample preparation and analysis system.

32. The sample analysis system of Clause 31, wherein the automated nucleic acid sample preparation and analysis system comprises a thermocycler.

33. The sample analysis system of Clause 32, wherein the automated nucleic acid sample preparation and analysis system comprises a real-time nucleic acid amplification and detection system.

34. A reaction vessel system, comprising:
a reaction vessel (RV) comprising:
a reaction chamber comprising a top opening and a closed bottom;
a RV cap comprising:
a cap body; and
a RV plug projecting downward from the cap body, the RV plug having a lower convex surface and sized for insertion into and sealing of the reaction chamber of the RV;
wherein, when the RV cap is inserted into the RV and a reaction mixture is present in the reaction chamber:
the lower convex surface of the RV plug reduces the void volume within the reaction chamber and displaces the air that makes up the void volume to a circumferential space defined by the lower convex surface of the RV plug and the upper surface of the reaction mixture within the reaction chamber.

35. The reaction vessel system of Clause 34, wherein when the RV cap is inserted into the RV and a reaction mixture is present in the reaction chamber, the lower convex surface of the RV plug contacts the upper surface of the reaction mixture.

36. The reaction vessel system of Clause 34 or Clause 35, wherein:
the RV comprises a groove disposed around the perimeter of the top opening, the groove comprising an outer groove wall, the outer groove wall comprising a radial groove disposed below an inward-projecting ridge on the outer groove wall; and
the RV cap comprises a lower wall projecting downward from the perimeter of the bottom of the cap body, the lower wall comprising an outer radial groove disposed above an outward projecting ridge of the lower wall,
wherein when the RV cap is fully inserted into the RV, the inward-projecting ridge on the outer groove wall of the RV is inserted into the outer radial groove of the RV cap; and the outward projecting ridge of the RV cap is inserted into the radial groove of the RV.

37. The reaction vessel of any one of Clauses 34 to 36, wherein the reaction chamber comprises a step that forms an upper region and a lower region of the reaction chamber, wherein the shape of the upper region is complementary to the shape of the RV plug.

38. The reaction vessel system of any one of Clauses 34 to 37, wherein the reaction chamber is sized to contain a reaction mixture having a volume of from 5 microliters to 100 microliters.

39. The reaction vessel system of any one of Clauses 34 to 38, wherein the RV cap is not integrated with the RV.

40. A method of capping a reaction vessel, comprising:
introducing a reaction mixture into a reaction chamber of a reaction vessel (RV); and
inserting a plug portion of a reaction vessel (RV) cap into the reaction chamber of the RV;
wherein the plug portion of the RV comprises a lower convex surface, and
wherein, during the inserting, the lower convex surface of the RV plug reduces the void volume within the reaction chamber and displaces the air that makes up the void volume to a circumferential space defined by the lower convex surface of the RV plug and the upper surface of the reaction mixture within the reaction chamber.

41. The method according to Clause 40, wherein when the plug portion of the RV cap is inserted into the reaction chamber of the RV, the lower convex surface of the RV plug contacts the upper surface of the reaction mixture.

42. The method according to Clause 40 or Clause 41, wherein introducing a reaction mixture into a reaction chamber of the RV comprises introducing a reaction mixture having a volume of from 5 microliters to 100 microliters.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A reaction vessel system, comprising:
a reaction vessel (RV) comprising:
a reaction chamber comprising a wall, a top opening, and a closed bottom;
a groove disposed around the perimeter of the top opening of the reaction chamber, the groove comprising:
an outer groove wall disposed radially outward relative to the top opening, and
an inward-projecting ridge, wherein the groove is disposed below the inward-projecting ridge on the outer groove wall;
a RV cap comprising:
a cap body comprising a pipettor barrel interface comprising an open top and a closed bottom;

a RV plug projecting downward from a central region of the bottom of the cap body, the RV plug sized for insertion into and sealing of the reaction chamber of the RV;

a lower wall projecting downward from the perimeter of the bottom of the cap body, the lower wall disposed radially outward relative to the bottom of the cap body and comprising an outward projecting ridge, wherein the lower wall is disposed above the outward projecting ridge of the lower wall, wherein, when the RV cap is inserted into the RV:
the RV plug of the RV cap is inserted into the reaction chamber of the RV;
the inward-projecting ridge on the outer groove wall of the RV is inserted into the outer radial groove of the RV cap; and
the outward projecting ridge of the RV cap is inserted into the radial groove of the RV.

2. The reaction vessel system of claim 1, wherein the RV cap is configured to seal the reaction chamber of the RV.

3. The reaction vessel system of claim 1, wherein the top opening of the RV is circular.

4. The reaction vessel system of claim 1, wherein the reaction chamber is conical.

5. The reaction vessel system of claim 1, wherein the reaction chamber has a round bottom.

6. The reaction vessel system of claim 1, wherein the reaction chamber further comprises a step that forms an upper region and a lower region of the reaction chamber, wherein the shape of the upper region is complementary to the shape of the RV plug.

7. The reaction vessel system of claim 1, wherein the reaction chamber is configured to be sized to contain a reaction mixture having a volume of from 5 microliters to 1 milliliter.

8. The reaction vessel system of claim 7, wherein the reaction chamber is configured to be sized to contain a reaction mixture having a volume of from 5 microliters to 500 microliters.

9. The reaction vessel system of claim 8, wherein the reaction chamber is configured to be sized to contain a reaction mixture having a volume of from 5 microliters to 100 microliters.

10. The reaction vessel system of claim 1, wherein the bottom surface of the reaction vessel is flat.

11. The reaction vessel system of claim 1, wherein the pipettor barrel interface comprises a step that forms an upper region and a lower region of the interface, wherein the reaction vessel system further comprises a pipettor barrel, and wherein the shape of the upper and lower regions is complementary to the shape of the pipettor barrel.

12. The reaction vessel system of claim 1, wherein the RV plug comprises an internal cavity.

13. The reaction vessel system of claim 1, wherein the RV plug has a lower convex surface.

14. The reaction vessel system of claim 13, wherein when the RV cap is inserted into the RV and a reaction mixture is present in the reaction chamber:
the lower convex surface of the RV plug is configured to reduce the void volume within the reaction chamber and displace the air that makes up the void volume to a circumferential space defined by the lower convex surface of the RV plug and the upper surface of the reaction mixture within the reaction chamber.

15. The reaction vessel system of claim 1, wherein the RV cap is not integrated with the RV.

16. The reaction vessel system of claim 1, wherein the RV cap is mated to the RV.

17. The reaction vessel system of claim 1, comprising a pipettor barrel mated with the pipettor barrel interface of the RV cap.

18. A sample analysis system, comprising:
the reaction vessel system of claim 1;
a robotic pipettor; and
a plurality of pipette tips, each of the plurality of pipette tips comprising a pipettor barrel interface sized and shaped to mate with a barrel of the pipettor,
wherein the pipettor barrel interface of the RV cap resembles the pipettor barrel interface of each of the plurality of pipette tips.

19. The sample analysis system of claim 18, wherein the robotic pipettor comprises from 1 to 10 pipettor barrels.

20. The sample analysis system of claim 18, wherein the system is an automated nucleic acid sample preparation and analysis system and comprises a thermocycler.

21. A reaction vessel system, comprising:
a reaction vessel (RV) comprising:
a reaction chamber comprising a wall, a top opening, and a closed bottom;
a groove disposed around the perimeter of the top opening of the reaction chamber, the groove comprising:
an outer groove wall disposed radially outward relative to the top opening, and
an inward-projecting ridge, wherein the groove is disposed below the inward-projecting ridge on the outer groove wall;
a RV cap comprising:
a cap body comprising a pipettor barrel interface comprising an open top and a closed bottom;
a lower wall projecting downward from the perimeter of the bottom of the cap body, the lower wall disposed radially outward relative to the bottom of the cap body and comprising an outward projecting ridge, wherein the lower wall is disposed above the outward projecting ridge of the lower wall; and
a RV plug projecting downward from the cap body, the RV plug having a lower convex surface and sized for insertion into and sealing of the reaction chamber of the RV;
wherein, when the RV cap is inserted into the RV and a reaction mixture is present in the reaction chamber:
the lower convex surface of the RV plug is configured to reduces the void volume within the reaction chamber and displaces the air that makes up the void volume to a circumferential space defined by the lower convex surface of the RV plug and an upper surface of the reaction mixture within the reaction chamber.

22. The reaction vessel system of claim 21, wherein when the RV cap is configured to be inserted into the RV when a reaction mixture is present in the reaction chamber, the lower convex surface of the RV plug is configured to contacts the upper surface of the reaction mixture.

23. The reaction vessel system of claim 21,
wherein when the RV cap is inserted into the RV, the inward-projecting ridge on the outer groove wall of the RV is inserted into the outer radial groove of the RV cap; and
the outward projecting ridge of the RV cap is inserted into the radial groove of the RV.

24. The reaction vessel system of claim 21, wherein the reaction chamber further comprises a step that forms an upper region and a lower region of the reaction chamber, wherein the shape of the upper region is complementary to the shape of the RV plug.

25. The reaction vessel system of claim 21, wherein the reaction chamber is configured to be sized to contain a reaction mixture having a volume of from 5 microliters to 100 microliters.

26. The reaction vessel system of claim 21, wherein the RV cap is not integrated with the RV.

* * * * *